United States Patent [19]

Jones

[11] 3,959,253

[45] May 25, 1976

[54] β-D-GLUCOSYLURONIC ACID DERIVATIVES

[75] Inventor: Howard Jones, Holmdel, N.J.

[73] Assignee: Merck & Co., Inc., Rahway, N.J.

[22] Filed: July 2, 1973

[21] Appl. No.: 376,014

[52] U.S. Cl. .............................. 260/210 R; 424/180
[51] Int. Cl.² ............................................ C07C 13/04
[58] Field of Search ......... 260/209, 210 R, 210 AB, 260/240 R, 345.7, 234 R

[56] References Cited
UNITED STATES PATENTS

| | | | |
|---|---|---|---|
| 3,316,260 | 4/1967 | Shen .............................. | 260/209 R |
| 3,629,238 | 12/1971 | Arasaki et al. .................. | 260/210 R |
| 3,658,786 | 4/1972 | Albrecht et al. ................ | 260/209 R |
| 3,699,103 | 10/1972 | Kiss................................... | 260/210 |
| 3,758,455 | 9/1973 | Masahiko........................ | 260/210 R |
| 3,812,109 | 5/1974 | Shen et al. ...................... | 260/240 R |

*Primary Examiner*—Johnnie R. Brown
*Attorney, Agent, or Firm*—Mario A. Monaco; Harry E. Westlake, Jr.

[57] ABSTRACT

Process for preparing β-D-glucosyluronic acid derivatives of pharmaceutical acids by the controlled hydrolysis of the corresponding 2,3,4-tri-O-acyl β-D-glucopyranosidyl uronate esters of the free acids.

6 Claims, No Drawings

β-D-GLUCOSYLURONIC ACID DERIVATIVES

DESCRIPTION OF THE INVENTION

This invention relates to a novel process for preparing β-D-glucosyluronic acid derivatives of pharmaceutical compounds containing an acid function, by the controlled acid hydrolysis of the 2,3,4-tri-O-acyl-β-D-glucopyranoside uronate ester of said pharmaceutical acids and to certain novel intermediates. More specifically, this invention relates to a process for preparing the β-D-glucosyluronic acid derivatives of 5-fluoro-2-methyl-1-(p-methylsulfinylbenzylidene)-indenyl-3-acetic acid, 5-fluoro-2-methyl-1-(p-methylsulfonylbenzylidene)-indenyl-3-acetic acid, 5-methoxy-2-methyl-1-(p-chlorobenzylidene)-indenyl-3-acetic acid, 4-amino-2-hydroxybenzoic acid, o-hydroxybenzoic acid, p-(dipropylsulfamoyl)benzoic acid, [2,3-dichloro-4-(2-methylenebutynyl)-phenoxy] acetic acid, pyridine-3-carboxylic acid and trans-4-(aminomethyl)-cyclohexane-carboxylic acid. Some of these acid derivatives are novel products; namely, the β-D-glucosyluronic acids of 5-fluoro-2-methyl-1-(p-methylsulfonylbenzylidene)-indenyl-3-acetic acid, 5-methoxy-2-methyl-1-(p-chlorobenzylidene)-indenyl-3-acetic acid, 4-amino-2-hydroxybenzoic acid, o-hydroxybenzoic acid, p-(dipropylsulfamoyl)benzoic acid, [2,3-dichloro-4-(2-methylenebutynyl)-phenoxy] acetic acid, pyridine-3-carboxylic acid and trans-4-(aminomethyl)-cyclohexane-carboxylic acid and make up still another part of this invention.

One of the urinary metabolites of the above mentioned acids are the β-D-glucosyluronic acid derivatives. These metabolites possess the same pharmaceutical utility as their free acid precursors. These metabolites are therefore useful as anti-inflammatory agents (5-fluoro-2-methyl-1-(p-methylsulfinylbenzylidene)-indenyl-3-acetic acid, 5-fluoro-2-methyl-1-(p-methylsulfonylbenzylidene)-indenyl-3-acetic acid and 5-methoxy-2-methyl-1-(p-chlorobenzylidene)-indenyl-3-acetic acid) 50–500 mg./day, for treatment of tuberculosis (4-amino-2-hydroxybenzoic acid) 8–12 gm./day, analgesics (o-hydroxybenzoic acid) 1–6 gm./day, uricosuric agent in gout (p-(dipropylsulfamoyl)benzoic acid) 0.25–2.0 gm./day, diuretic ([2,3-dichloro-4-(2-methylenebutynyl)-phenoxy] acetic acid) 50–200 mg./day, cholesteral synthesis inhibitor (pyridine-3-carboxylic acid) 3–6 gm./day or anti-fibrinolytic agent (trans-4-(aminomethyl)-cyclohexane carboxylic acid) 6–10 gm./day. These metabolites can be administered to patients in the same manner and under the same conditions as their corresponding known and useful free acid drugs.

BACKGROUND OF THE INVENTION

In the past, it has been virtually impossible to obtain these metabolites in substantially pure form so that they would be useful as drugs for the same intended use as their precursor acids. Heretofore, these metabolites have been only indirectly shown to exist in human urinary waste by the complete hydrolysis of the metabolites in the urine and the chemical determination of their component parts.

DETAILS OF THE INVENTION

I have found a direct and practical synthesis for the preparation of these metabolites wherein they can be readily isolated in substantially pure form suitable for pharmaceutical use. It is therefore an object of this invention to prepare the above mentioned metabolities and especially the metabolities of 5-fluoro-2-methyl-1-(p-methylsulfinylbenzylidene)-indenyl-3-acetic acid and 5-fluoro-2-methyl-1-(p-methylsulfonylbenzylidene)-indenyl-3-acetic acid by a simple and practical chemical synthesis. It is also an object of this invention to prepare these metabolities in sufficiently pure form to allow their application as pharmaceutical agents as described above.

The following literature references, D. Keglevic, N. Pravdic and J. Tomasio, *J. Chem. Soc.* (1968), page 511; D. Keglevic and M. Pokorny, *Biochem. J.* 114 (1969) 827 and preceeding papers and R. Bugianesi and T. Y. Shen, Carb. Res. 19, 179 (1971) describe the preparation of certain uronates of particular acids by methods which are either cumbersome and/or lead to mixtures of products. On the other hand, I have found that in the present process substantially pure metabolites in good yield are readily obtained. The glucosidic linkage has been known to be extremely sensitive to basic hydrolytic conditions. However, I have surprisingly found that this linkage has some stability to acidic conditions in comparison to the ease of hydrolysis of the pyranosyl acyloxy and ester functions of these metabolites. More specifically, I have found that under the particularly controlled acid conditions used in the process of our invention, the β-D-glucosyluronic acid derivatives of the above mentioned acids are readily obtained in good yield.

Using the process for preparing [5-fluoro-2-methyl-1-(p-methylsulfinylbenzylidene)-indenyl-3-acetyl]-β-D-glucopyrosidyluronic acid, as an example, the process of this invention entails the preparation of this compound by the hydrolysis of the corresponding [5-fluoro-2-methyl-1-(p-methylsulfinylbenzylidene)-indenyl-3-acetyl]-2,3,4-tri-O-acyl-β-D-glucopyranosidyl uronate ester. The uronate ester may readily be any desired ester since the ester moiety comes off during the reaction and therefore is not critical to the invention. Accordingly, one may use a substituted or unsubstituted $C_{1-5}$ alkyl ester, phenyl ester or Ar-$C_{1-5}$ alkyl ester such as benzyl, but preferably a $C_{1-5}$ alkyl ester and especially methyl or ethyl is employed. Similarly, since the acyl group on the uronate ester is removed during the reaction and the particular group is not critical to the invention, one may use any acyl group such as substituted or unsubstituted $C_{1-5}$ alkanoyl, particularly formyl or acetyl or substituted or unsubstituted Ar-$C_{1-5}$ alkanoyl such as benzoyl or phenacetyl, but preferably one uses $C_{1-5}$ alkanoyl and especially acetyl.

The reaction is carried out under acidic hydrolysis conditions. More specifically, the uronate ester is reacted with an organic or inorganic acid in the presence of a solvent. The organic acid may suitably be a haloalkanoic acid of from 2 to 5 carbon atoms such as trichloroacetic, bromoacetic, trifluoroacetic or propionic acid or an inorganic acid such as phosphoric acid, fluorosulfonic acid or mineral acid such as hydrobromic or hydrochloric acid. The acid employed is preferably used in the form of an aqueous solution and preferably hydrochloric or hydrobromic acid is used. The normality of the acid solution is preferably between 0.5 to 4.0 normal. The mole ratio of acid to ester and the normality of the reaction mixture is an important aspect of this invention, in that certain limits are necessary to obtain appropriate hydrolysis without substantial side products. Accordingly, the mole ratio of acid or ester should be between about 4 to about 15 moles of acid to 1 mole of ester and the normality of the total reaction mixture should be between about 0.5 to 1.5 normal. Preferably, the mole ratio of acid to ester is 6 to 9 and the normality of the reaction mixture 0.6 to 1.0. The reaction is further carried out in the presence of a polar solvent such as ethers (dimethoxyethylether, methoxyethylether, methoxyethanol, tetrahydrofuran or ethoxyethanol), $C_{1-5}$ alkanols (methanol, ethanol, isopropanol, butanol), $C_{1-3}$ alkylamides (formamide), di-$C_{2-6}$ alkylsulfoxides (dimethylsulfoxide) and the like. Preferably, the solvent employed is one boiling lower than water, such as tetrahydrofuran or an alkanol. Although any suitable amount of solvent may be used, it is preferred that no more solvent be used than is required to dissolve the ester reactant at room temperature. The reaction is carried out at a temperature of about 60° to 100° and preferably from about 75° to 95°C for a period of about 1 to 6 hours and preferably from about 2 to 4 hours. After the reaction is complete, isolation is carried out by known techniques, although it is preferred to isolate the product in the following manner:

Between 30 and 60% of the organic solvent is evaporated from the reaction mixture and in those cases wherein a solvent boiling higher than water is employed, no evaporation is carried out since the amount of solvent used therein is preferably no more than is needed to dissolve the ester at room temperature. At this point, the reaction mixture is then extracted with any non-polar solvent such as methylene chloride, ether, benzene, toluene, chloroform or carbon tetrachloride. The extraction is preferably carried out between 1 and 3 times and especially 2 to 3 times using between 1 to 6 mls. of solvent per gram of ester each time and especially 2 to 4 mls. The remaining solution after extraction is salted out by any well known means such as with alkali or alkali earth halides (NaCl, KCl, CaCl$_2$) at or near the saturation point of the solution (85–100%). The saturated solution is then extracted with polar solvents only partially or nonmiscible with water such as chloroform, carbon tetrachloride or ethylacetate until the desired product is substantially extracted.

The procedure described above may be suitably used to prepare the other β-D-glucosyluronic acids of this invention by employing [5-fluoro-2-methyl-1-(p-methylsulfonylbenzylidene)-indenyl-3-acetyl]-2,3,4-tri-O-acyl-β-D-glucopyranosidyl uronate ester, [5-ethoxy-2-methyl-1-(p-chlorobenzylidene)-indenyl-3-acetyl]-2,3,4-tri-O-acyl-β-D-glucopyranosidyl uronate ester, (4-amino-2-hydroxy-1-carboxyphenyl)-2,3,4-tri-O-acyl-β-D-glucopyranosidyl uronate ester, (2-hydroxy-1-carboxyphenyl)-2,3,4-tri-O-acyl-β-D-glucopyranosidyl uronate ester, [4-(dipropylsulfamoyl)-1-carboxyphenyl]-2,3,4-tri-O-acyl-β-D-glucopyranosidyl uronate ester, [3-dichloro-4-(2-methylenebutynyl)-phenoxy]-acetyl-2,3,4-tri-O-acyl-β-D-glucopyranosidyl urnate ester, (pyridine-3-carboxy)-2,3,4-tri-O-acyl-β-D-glucopyranosidyl uronate ester and trans-[4-(aminomethyl)cyclohexane]-carboxy-2,3,4-tri-O-acyl-β-D-glucopyranosidyl uronate ester. These intermediates are novel products and make up another part of this invention. The 2,3,4-tri-O-acyl-β-D-glucopyranosidyl uronate ester used in the above procedure is, in turn, obtained by reacting the acid or preferably the salt of the starting pharmaceutical acid such as 5-fluoro-2-methyl-1-(p-methylsulfinylbenzylidene)-indenyl-3-acetic acid with a 2,3,4-tri-O-acyl-1-halo-1-deoxy-β-D-glucopyronurate ester in the presence of an inert solvent. The reaction is preferably carried out upon the salt of the acid such as the alkali or alkali earth metal salt (Na, K, Ca), NH$_4$$^+$ or $C_{1-5}$ alkyl NH$_4$$^+$ (tetramethyl NH$_4$$^+$) or benzyl-tri-$C_{1-5}$ alkyl NH$_4$$^+$ salt and especially the alkali salt such as sodium or potassium. One can however, if desired, prepare the salt of the acid in situ followed by the reaction with the α-D-glucopyronurate. The α-D-glucopyronurate employed may be any tri-O-acyl derivative whose acyl is as described previously, but preferably the tri-O-acetyl or formyl derivative; the halo substituent may be bromo or chloro but preferably bromo, and ester moiety may be any of those as previously described but preferably the methyl ester. Accordingly, the preferred reactant is methyl 2,3,4-tri-O-acetyl (or formyl)-1-bromo-1-deoxy-α-D-glucopyronurate. This compound or its other derivatives mentioned can be readily prepared as described in *J. Amer. Chem. Soc.* 82, 2827 (1960). The reaction is suitably carried out by reacting the acid salt and glucopyronurate ester in the presence of one of the inert solvents as described previously for the reaction of the uronate ester and especially a solvent substantially free of water, at a temperature of from about 0° to about 100°C, preferably about room temperature to about 75°C and especially about 50° to 65°C for a reaction time of from 1 to 10 hours and preferably 1 to 4 hours. The concentration of glucopyronurate ester to acid salt may be between about 0.5 moles to about 5.0 moles preferably 1.0 to 3.0 moles and especially 1.5 to 2.0 moles. Although the amount of solvent used is not critical, one would normally employ between 1 to 100 ml. of solvent per gram of reactants preferably 1 to 10 ml. of solvent and especially 1 to 5 ml. of solvent. Following reaction, the glucopyranosidyl uronate ester mixture may be employed directly in the next reaction step or preferably the glucopyranosidyl uronate is first isolated. The isolation of the crude product may be carried out by reducing the total volume of reaction mixture by from 20 to 70% and preferably 40 to 50%, dissolving the residue in water and extracting the aqueous solution with a suitable solvent such as chloroform, ethylacetate, methylene chloride or carbon tetrachloride. The crude product may then be used directly in the next reaction as described previously.

The following examples are given by way of illustration:

EXAMPLE 1

Sodium 5-fluoro-2-methyl-1-(p-methylsulfinylbenzylidene)-indenyl-3-acetate 5-fluoro-2-methyl-1-(p-methylsulfinylbenzylidene)indenyl-3-acetic acid.

To a stirred solution of the 12.0 g. (0.033 mole) in THF (200 ml.) is added 74 ml. of a 25% solution of NaOMe in water. The ppt is aged for 4 hours and filtered. The sodium salt is dried over $P_2O_5$ at 100° for 24 hours.

Similarly when potassium or calcium methoxide or ammonium hydroxide is used in the above example in place of sodium methoxide, the corresponding potassium, calcium or ammonium acetate compound is obtained.

Similarly when 5-fluoro-2-methyl-1-(p-methylsulfonylbenzylidene)-indenyl-3-acetic acid, 5-methoxy-2-methyl-1-(p-chlorobenzylidene)-indenyl-3-acetic acid, 4-amino-2-hydroxybenzoic acid, o-hydroxybenzoic acid, p-(dipropylsulfamoyl)benzoic acid, [2,3-dichloro-4-(2-methylenebutynyl)-phenoxy] acetic acid, pyridine-3-carboxylic acid or trans-4-(aminomethyl)-cyclohexane carboxylic acid is used in place of the sulfinyl compound in Example 1, there is obtained their corresponding sodium salts.

EXAMPLE 2

Methyl [5-fluoro-2-methyl-1-(p-methylsulfinylbenzylidene)-indenyl-3-acetyl]-2,3,4-tri-O-acetyl-$\beta$-D-glucopyranosidyl uronate A solution of sodium 5-fluoro-2-methyl-1-(p-methylsulfinylbenzylidene)-indenyl-3-acetate 9.7 g. in 50 ml. dry DMSO and 12.0 g. of methyl 2,3,4-tri-O-acetyl-1-bromo-1-deoxy-$\alpha$-D-glucopyronurate in 50 ml. dry DMSO is heated together with stirring for 2 hours at 60°.

About 50 ml. of DMSO was evaporated off under high vacuum and the residue was dissolved in 100 ml. hot water. The aqueous solution is extracted with $CHCl_3$ and the dried solvent removed in vacuo to give crude glucuronate ester (13.4 g.) which is not further purified.

Similarly when an equivalent amount of the potassium, calcium or ammonium salt obtained from Example 1 is used in place of the sodium salt in Example 2, there is obtained the product of Example 2.

Similarly when the sodium salts of 5-fluoro-2-methyl-1-(p-methylsulfonylbenzylidene)-indenyl-3-acetic acid, 5-methoxy-2-methyl-1-(p-chlorobenzylidene)-indenyl-3-acetic acid, 4-amino-2-hydroxybenzoic acid, o-hydroxybenzoic acid, p-(dipropylsulfamoyl)bonzoic acid, [2,3-dichloro-4-(2-methylenebutynyl)-phenoxy]-acetic acid, pyridine-3-carboxylic acid or trans-4(aminomethyl)-cyclohexane carboxylic acid are used in place of the sulfinyl compound in Example 2, there are obtained the corresponding glucopyranosidyl uronates.

EXAMPLE 3

[5-fluoro-2-methyl-1-(p-methylsulfinylbenzylidene)-indenyl-3-acetyl]-$\beta$-D-glucopyranosidyluronic acid The crude methyl [5-fluoro-2-methyl-1-(p-methylsulfinylbenzylidene)-indenyl-3-acetyl]-2,3,4-tri-O-acetyl-$\beta$-D-glucopyranosidyl uronate 13.0 g. is dissolved in 125 ml. dimethoxyethane and stirred with 62.5 ml. of 2.5 N HCl at 90° for 3 hours. The reaction mixture is evaporated to ½ volume at 70° and extracted with $CH_2Cl_2$ (2 × 30 ml.). The remaining solution is then saturated with NaCl and extracted with $CH_2Cl_2$ (30 ml.), EtoAc (2 × 50 ml.). The EtoAc layers are washed with water (20 ml.), dried ($MgSO_4$), filtered and evaporated to give pure glucuronic acid (2; 1.4 g.) m.p. 170°–172° Anal. ($C_{26}H_{25}SFO_9.H_2O$) C, H, S, F. After drying under vacuo at 120° for 2 hours Anal. ($C_{26}H_{25}SFO_9$) C, H.

Similarly when the glucopyranosidyl uronates obtained from Example 2 are used in place of the uronate ester in Example 3 above, ther is obtained the corresponding $\beta$-D-glucopyrosidyl acids.

EXAMPLE 4

5-fluoro-2-methyl-1-(p-methylsulfonylbenzylidene)-indenyl-3-acetic acid m-Chloroperbenxoic acid 0.46 g. (0.294 mole) is added all at once to a stirred solution of 5-fluoro-2-methyl-1-(p-methylsulfinylbenzylidene)-indenyl-3-acetic acid 1.0 g. (0.284 mole) in $Me_2CO$ at room temperature. After 1 hour the reaction mixture is evaporated to dryness and washed well with boiling water (200 ml.). The product is filtered and reextracted from ethyl acetate (0.85 g.) m.p. 194°–196° Anal. ($C_{20}H_{17}SFO_4$) C, H, S, F.

EXAMPLE 5

[5-fluoro-2-methyl-1-(p-methylsulfonylbenzylidene)-indenyl-3-acetyl]-$\beta$-D-glucopyranosyluronic acid The reactions described in Examples 1 to 3 are repeated on the sulfonyl acid (18.2 g.) to give 32 g. of crude ester sulfone. The hydrolytic cleavage and isolation is then followed as shown in Example 3 to give the glucuronic acid (700 mg.) m.p. 177°–178° (dec.) Anal. ($C_{26}H_{25}SFO_{10}.H_2O$) C, H, S, F.

What is claimed is:

1. A process for preparing 1-O-$\beta$-D-glucopyranosyluronic acid ester of:
   a. 5-fluoro-2-methy-1-(p-methylsulfinylbenzylidene) indenyl-3-acetic acid;
   b. 5-fluoro-2-methyl-1-(p-methylsulfonylbenzylidene) indenyl-3-acetic acid;
   c. 5-methoxy-2-methyl-1-(p-chlorobenzylidene)-indenyl-3-acetic acid;
   d. 4-amino-2-hydroxybenzoic acid;
   e. 2-hydroxybenzoic acid;
   f. p-(dipropylsulfamoyl) benzoic acid;
   g. [2,3-dichloro-4-(2-methylenebutynyl)phenoxy]-acetic acid;
   h. pyridine-3-carboxylic acid; or
   i. trans-4-(aminomethyl) cyclohexanecarboxylic acid; which comprises hydrolyzing the corresponding 2,3,4-tri-O-acetyl-1-O-$\beta$D-glucopyranosyluronate esters in a polar solvent in the presence of an acid, wherein the mole ratio of acid to ester starting material is about 4 to 15, and the normality of the total reaction mixture is between 0.5 and 1.5.

2. The process of claim 1 wherein the mole ratio is about 6 to about 9, the normality of the reaction mixture is between about 0.6 to about 1.0 and the temperature of reaction is between about 60°C to about 100°C.

3. The process of claim 1 wherein the uronate ester is the 2,3,4-tri-$C_{1-5}$ alkyl ester.

4. The process of claim 2 wherein the uronate ester is selected from the group consisting of methyl-[5-fluoro-2-methyl-1-(p-methylsulfinylbenzylidene)-indenyl-3-acetyl]-2,3,4-tri-O-acetyl-$\beta$-D-glucopyranosidyl uronate or methyl-[5-fluoro-2-methyl-1-(p-methylsulfonylbenzylidene)-indenyl-3acetyl]-2,3,4-tri-o-acetyl-$\beta$-D-glucopyranosidyl uronate.

5. The process of claim 2 wherein the polar solvent is selected from the group consisting of an ether, $C_{1-5}$ alkanol, $C_{1-3}$ alkylamide or di-$C_{2-6}$ alkylsulfoxide.

6. A compound selected from the group consisting of the $\beta$-D-glucopyrosidyluronic acids of [5-fluoro-2-methyl-1-(p-methylsulfinylbenzylidene)-indenyl-3-acetic acid, 5-fluoro-2-methyl-1-(p-methylsulfonylbenzylidene)-indenyl-3-acetic acid,] 5-methoxy-2-methyl-1-(p-chlorobenzylidene)-indenyl-3-acetic acid, 4-amino-2-hydroxybenzoic acid, o-hydroxybenzoic acid, p-(dipropylsulfamoyl)benzoic acid, (2,3-dichloro-4-(2-methylenebutynyl)-phenoxy) acetic acid, pyridine-3-carboxylic acid or trans-4-(aminomethyl)-cyclohexane carboxylic acid.

* * * * *

UNITED STATES PATENT OFFICE
CERTIFICATE OF CORRECTION

PATENT NO. : 3,959,253
DATED : May 25, 1976
INVENTOR(S) : Howard Jones

PAGE 1 of 2

It is certified that error appears in the above-identified patent and that said Letters Patent are hereby corrected as shown below:

The title appearing in column 1 which reads as:

"> -D-GLUCOSYLURONIC ACID DERIVATIVES"

should be corrected as follows:

"β-D-GLUCOSYLURONIC ACID DERIVATIVES"

Column 3, line 3, "or" should be changed to "to".

Column 5, line 40, "bonzoic" should be changed to "benzoic".

Column 5, line 41, "bonzoic" should be deleted.

Column 5, line 67 "ther" should be changed to "there".

Column 6, line 5, "m-Chloroperbenxoic" should be changed to "m-Chloroperbenzoic".

Column 6, line 25, "ester" should be changed to "esters".

Column 6, line 39, "βD" should be changed to "β-D".

UNITED STATES PATENT OFFICE
CERTIFICATE OF CORRECTION

PATENT NO. : 3,959,253
DATED : May 25, 1976
INVENTOR(S) : Howard Jones

It is certified that error appears in the above-identified patent and that said Letters Patent are hereby corrected as shown below:

PAGE 2 OF 2

Column 6, Claim 3, which reads:

"The process of claim 1 wherein the uronate ester is the 2,3,4-tri-$C_{1-5}$ alkyl ester."

should be changed as follows:

"The process of claim 1 wherein the uronate ester is the 2,3,4-tri-$C_{1-5}$alkanoyl $C_{1-5}$alkyl ester."

Column 6, Claim 6, "[5-fluoro-2-methyl-1-(p-methylsulfinylbenzylidene)-indenyl-3-acetic acid, 5-fluoro-2-methyl-1-(p-methylsulfonylbenzylidene)-indenyl-3-acetic acid,]" should be deleted.

Signed and Sealed this

Thirtieth Day of November 1976

[SEAL]

Attest:

RUTH C. MASON
Attesting Officer

C. MARSHALL DANN
Commissioner of Patents and Trademarks